United States Patent [19]

Eidenschink et al.

[11] Patent Number: 4,617,140
[45] Date of Patent: Oct. 14, 1986

[54] BICYCLOHEXYL DERIVATIVES

[75] Inventors: Rudolf Eidenschink; Joachim Krause, both of Dieburg, Fed. Rep. of Germany

[73] Assignee: Merck Patent Gesellschaft mit beschrankter Haftung, Darmstadt, Fed. Rep. of Germany

[21] Appl. No.: 760,233

[22] Filed: Jul. 29, 1985

Related U.S. Application Data

[63] Continuation of Ser. No. 468,736, Feb. 22, 1983, abandoned.

[30] Foreign Application Priority Data

Feb. 20, 1982 [DE] Fed. Rep. of Germany ....... 3206269

[51] Int. Cl.$^4$ ........................... G02F 1/13; C09K 3/34; C07C 69/753; C07C 69/757; C07D 319/06
[52] U.S. Cl. ........................... 252/299.61; 252/299.5; 252/299.63; 350/350 R; 350/350 S; 549/369; 549/374; 549/375; 560/59; 560/61; 560/72; 560/73; 560/101; 560/118; 560/126; 560/129; 560/227; 560/228
[58] Field of Search ...................... 252/299.63, 299.61, 252/299.5; 350/350 R, 350 S; 549/369; 560/118, 126, 227, 228, 129, 61, 72, 73, 59, 101; 549/374, 375

[56] References Cited

U.S. PATENT DOCUMENTS

| | | | |
|---|---|---|---|
| 4,181,625 | 1/1980 | Eidenschine et al. | 252/299.63 |
| 4,229,315 | 10/1980 | Krause et al. | 252/299.63 |
| 4,261,652 | 4/1981 | Gray et al. | 252/299.62 |
| 4,330,426 | 5/1982 | Eidenschine et al. | 252/299.63 |
| 4,340,498 | 7/1982 | Sugimori et al. | 252/299.63 |
| 4,348,324 | 9/1982 | Demus et al. | 252/299.61 |
| 4,349,452 | 9/1982 | Osman et al. | 252/299.63 |
| 4,361,494 | 11/1982 | Osman et al. | 252/299.63 |
| 4,382,012 | 5/1983 | Eidenschine et al. | 252/299.63 |
| 4,387,039 | 6/1983 | Sugimori et al. | 252/299.63 |
| 4,398,803 | 8/1983 | Poal et al. | 252/299.01 |
| 4,410,445 | 10/1983 | Baur et al. | 252/299.5 |
| 4,438,268 | 3/1984 | Zaschke et al. | 252/299.62 |
| 4,452,719 | 6/1984 | Inoue et al. | 252/299.63 |
| 4,507,222 | 3/1985 | Inoue et al. | 252/299.63 |

FOREIGN PATENT DOCUMENTS

| | | | |
|---|---|---|---|
| 56501 | 7/1982 | European Pat. Off. | 252/299.63 |
| 58981 | 9/1982 | European Pat. Off. | 252/299.63 |
| 69387 | 1/1983 | European Pat. Off. | 252/299.63 |
| 87102 | 8/1983 | European Pat. Off. | 252/299.63 |
| 90548 | 10/1983 | European Pat. Off. | 252/299.63 |
| 3211601 | 10/1983 | European Pat. Off. | 252/299.63 |
| 2636684 | 9/1980 | Fed. Rep. of Germany | 252/299.63 |
| 3237020 | 5/1983 | Fed. Rep. of Germany | 252/299.63 |
| 210920 | 6/1984 | German Democratic Rep. | 252/299.62 |
| 56-68636 | 6/1981 | Japan | 252/299.63 |
| 57-54137 | 3/1982 | Japan | 252/299.63 |
| 57-54148 | 3/1982 | Japan | 252/299.63 |
| 57-64645 | 4/1982 | Japan | 252/299.63 |
| 57-70839 | 5/1982 | Japan | 252/299.63 |
| 57-171936 | 10/1982 | Japan | 252/299.63 |
| 57-209252 | 12/1982 | Japan | 252/299.63 |
| 58-55447 | 4/1983 | Japan | 252/299.63 |

*Primary Examiner*—Teddy S. Gron
*Attorney, Agent, or Firm*—Millen & White

[57] ABSTRACT

Bicyclohexyl derivatives of formula I $$R^1-Cy-Cy-X-Y \qquad \text{I}$$

wherein
X is —CO—O— or —O—CO—,
Y is alkyl or perfluoroalkyl in each case of 1–8 C atoms, —Cy—Cy—R$^2$, —Cy—Ph—R$^2$, —Ph—Cy—R$^2$, —Ph—Ph—R$^2$ or —Ph—Dio—R$^2$,
Cy is 1,4-cyclohexylene,
Ph is 1,4-phenylene,
Dio is 1,3-dioxane-2,5-diyl and
R$^1$ and R$^2$ are each alkyl or alkoxy in each case of 1–8 C atoms, can be used as components of liquid crystal dielectrics.

21 Claims, No Drawings

BICYCLOHEXYL DERIVATIVES

This is a continuation of application Ser. No. 468,736 filed Feb. 22, 1983, now abandoned.

This invention relates to new bicyclohexyl derivatives.

SUMMARY OF THE INVENTION

It is an object of this invention to provide new liquid crystal compounds which are suitable as components of liquid crystal dielectrics, in particular for nematic phases having a low optical anisotropy.

Upon further study of the specification and appended claims, further objects and advantages of this invention will become apparent to those skilled in the art.

These objects have been achieved by providing the new bicyclohexyl derivatives of formula I $$R^1-Cy-Cy-X-Y \qquad I$$

wherein
X is —CO—O— or —O—CO—,
Y is alkyl or perfluoroalkyl in each case of 1-18 C atoms, —Cy—Cy—$R^2$, —Cy—Ph—$R^2$, —Ph—Cy—$R^2$, —Ph—Ph—$R^2$ or —Ph—Dio—$R^2$,
Cy is 1,4-cyclohexylene,
Ph is 1,4-phenylene,
Dio is 1,3-dioxane-2,5-diyl and
$R^1$ and $R^2$ are each alkyl or alkoxy in each case of 1-8 C atoms.

These substances, like similar compounds, for example those known from German Offenlegungsschrift No. 2,800,553 (U.S. Pat. No. 4,229,315) whose disclosure is incorporated by reference herein, are useful as components of liquid crystal dielectrics, in particular for displays based on the principle of the twisted cell.

DETAILED DISCUSSION

It has been found that the compounds of formula I are outstandingly suitable as components of liquid crystal dielectrics. In particular, liquid crystal phases having a relatively low optical anisotropy, such as are required for twisted cells in the sub-Mauguin region to achieve a contrast which has little dependence on the angle (compare German Offenlegungsschrift No. 3,022,818 and its U.S. equivalent, Ser. No. 273,271 of June 15, 1981, whose disclosure is incorporated by reference herein), can be prepared using these compounds.

The compound of formula I are colorless in the pure state, and form liquid crystal mesophases in a temperature range which is favorably suitable for electrooptical use.

Those compounds of formula I which are optically active are suitable as chiral doping materials for the preparation of cholesteric phases such as can be used for White-Taylor dyestuff cells. Compared with the biphenyl derivatives which were hitherto customary, they have the advantages of a higher "twisting power" and a lower optical anisotropy; in low concentrations in the twisted cell these chiral compounds are able to prevent interference with the optical visible image by the "reverse twist" (compare Mol. Cryst. Liq. Cryst., volume 34 (Letters), pages 211-217 (1977)).

The invention thus relates to the compounds of formula I and to a process for their preparation, comprising reacting a carboxylic acid of formula II $$Q-COOH \qquad II$$

wherein Q is (a) $R^1$—Cy—Cy— or (b) Y, and $R^1$, Cy and Y are as defined above, or a reactive derivative thereof, with a hydroxy compound of formula III $$Z-OH \qquad III$$

wherein Z is (a) Y or (b) $R^1$—Cy—Cy—, and $R^1$, Cy and Y are as defined above, or a reactive derivative thereof, or to prepare compounds of formula I (Y=—Ph—Dio—$R^2$), reacting an aldehyde of formula IV $$R^1-Cy-Cy-X-Ph-CHO \qquad IV$$

wherein $R^1$, X, Ph and Cy are as defined above, with a diol of formula V $$(HOCH_2)_2-CH-R^2 \qquad V$$

wherein $R^2$ is as defined above.

The invention furthermore relates to the use of the compounds of formula I as components of liquid crystal dielectrics, liquid crystal dielectrics containing at least one compound of formula I, and electrooptical display elements which contain such dielectrics.

In the preceding and following text, X, Y, Cy, Ph, Dio, $R^1$, $R^2$, Q and Z are as defined above, unless expressly indicated otherwise.

The compounds of formula I include esters of the formula Ia and Ib

| | |
|---|---|
| $R^1$—Cy—Cy—CO—O—Y | Ia |
| $R^1$—Cy—Cy—O—CO—Y | Ib |

In detail, formula I includes esters of the following formulae Ic to Ip

| | |
|---|---|
| $R^1$—Cy—Cy—CO—O—alkyl | Ic |
| $R^1$—Cy—Cy—CO—O—perfluoroalkyl | Id |
| $R^1$—Cy—Cy—CO—O—Cy—Cy—$R^2$ | Ie |
| $R^1$—Cy—Cy—CO—O—Cy—Ph—$R^2$ | If |
| $R^1$—Cy—Cy—CO—O—Ph—Cy—$R^2$ | Ig |
| $R^1$—Cy—Cy—CO—O—Ph—Ph—$R^2$ | Ih |
| $R^1$—Cy—Cy—CO—O—Ph—Dio—$R^2$ | Ii |
| $R^1$—Cy—Cy—O—CO—alkyl | Ij |

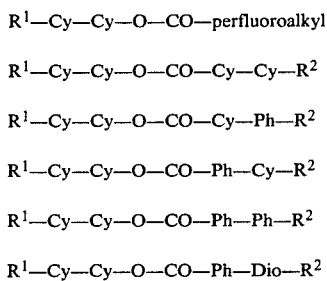

wherein the alkyl, perfluoroalkyl and alkoxy groups in each case contain 1–8, preferably 1–5 and in particular, 3, 4 or 5 C atoms.

The compounds of formula Ic, and furthermore those of the formulae Id to Ig, Ii, Ik to In and Ip are preferred.

The radicals $R^1$ and $R^2$ are preferably alkyl.

Of those compounds of formulae I to Ia to Ip, those stereoisomers in which the two substituents on the cyclohexylene and dioxanediyl radicals are in each case in the trans-position relative to one another are preferred.

In the compounds of formulae I and Ia to Ip, the alkyl, alkoxy and perfluoroalkyl groups are preferably straight-chain. Alkyl is thus preferably methyl, ethyl, n-propyl, n-butyl, n-pentyl, n-hexyl, n-heptyl or n-octyl; perfluoroalkyl is preferably trifluoromethyl, pentafluoroethyl, heptafluoropropyl, nonafluorobutyl, undecafluoropentyl, tridecafluorohexyl, pentadecafluoroheptyl or heptadecafluorooctyl; and alkoxy is preferably methoxy, ethoxy, n-propoxy, n-butoxy, n-pentyloxy, n-hexyloxy, n-heptyloxy or n-octyloxy.

Compounds of formulae I and Ia to Ip with branched alkyl, perfluoroalkyl or alkoxy groups may occasionally be of importance because they have a better solubility in the customary liquid crystal base materials, but in particular as chiral doping substances, if they are optically active. Branched groups of this type as a rule contain not more than one chain-branching. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptyl (=1-methylhexyl), 2-octyl (=1-methylheptyl); preferred branched alkoxy radicals are isopropoxy, 2-methylpropoxy, 2-methylbutoxy, 3-methylbutoxy, 2-methylpentyloxy, 3-methylpentyloxy, 2-ethylhexyloxy, 1-methylhexyloxy and 1-methylheptyloxy.

The compounds of formula I are otherwise prepared by methods which are known per se, such as those described in the literature (for example in the standard works, such as Houben-Weyl, Methoden der Ogranischen Chemie [Methods of Organic Chemistry], Georg-Thieme-Verlag, Stuttgart), and in particular under reaction conditions which are known and suitable for the mentioned reactions. Variants which are known per se and are not mentioned here in more detail can also be utilized.

If desired, the starting substances can also be formed in situ, in a manner such that they are not isolated from the reaction mixture, but are immediately further reacted to give the compounds of formula I.

Particularly suitable reactive derivatives of the carboxylic acids of formula II are the acid halides, above all the chlorides and bromides, and furthermore the anhydrides, for example also mixed anhydrides of the formula Q—CO—COCH$_3$, azides and esters, in particular alkyl esters with 1–4 C atoms in the alkyl group.

Particularly suitable reactive derivatives of the alcohols or phenols of formula III are the corresponding metal alcoholates and phenolates of the formula Z—OM in which M is one equivalent of a metal, preferably an alkali metal, such as Na or K.

The esterification is advantageously carried out in the presence of an inert solvent. Particularly suitable solvents are ethers, such as diethyl ether, di-n-butyl ether, tetrahydrofuran, dioxane or anisole, ketones, such as acetone, butanone or cyclohexanone, amides, such as dimethylformamide or phosphoric acid hexamethyltriamide, hydrocarbons, such as benzene, toluene or xylene, halogenohydrocarbons, such as carbon tetrachloride or tetrachloroethylene, and sulfoxides, such as dimethylsulfoxide or sulfolane. Water-immiscible solvents can at the same time advantageously be used for azeotropic distillation of the water formed during the esterification. An excess of an organic base, for example pyridine, quinoline or triethylamine, may also occasionally be used as the solvent for the esterification. The esterification can also be carried out in the absence of a solvent, for example by simply heating the components in the presence of sodium acetate.

The reaction temperature is usually −50° to +250°, preferably −20° to +80°. At these temperatures, the esterification reactions have as a rule ended after 15 minutes to 48 hours.

In detail, the reaction conditions for the esterification substantially depend on the nature of the starting substances used. Thus, a free carboxylic acid of formula II is as a rule reacted with an alcohol or phenol of formula III in the presence of a strong acid, for example as mineral acid, such as hydrochloric acid or sulfuric acid.

A preferred reaction procedure is the reaction of an acid anhydride or, in particular, an acid chloride with an alcohol, preferably in a basic medium, in which case bases of particular importance are alkali metal hydroxides, such as sodium or potassium hydroxide, alkali metal carbonates or bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline.

A further preferred embodiment of the process according to this invention comprises first converting the hydroxy commpound of formula III to be esterified into the sodium alcoholate or phenolate or potassium alcoholate or phenolate, for example by treatment with ethanolic sodium hydroxide solution or potassium hydroxide solution, isolating this product and suspending it in acetone or diethyl ether, together with sodium bicarbonate or potassium carbonate, while stirring, and adding a solution of the acid chloride or anhydride in diethyl ether, acetone or dimethylformamide to this suspension, preferably at temperatures of about −25° to +20°.

To prepare the phenyldioxane derivatives of formula I (Y=—Ph—Dio—R²), it is also possible to acetalize an aldehyde of formula IV with a diol of formula V, preferably in the presence of an inert solvent, such as benzene or toluene, and/or a catalyst, for example a strong acid, such as sulfuric acid or benzene- or p-toluene-sulfonic acid, at temperatures of about 20° to about 150°, preferably 80° to 120°.

Most of the starting substances of the formulae II to V and their reactive derivatives are known; these and all of the new such compounds can be prepared routinely from compounds which are known from the literature using fully conventional methods of organic chemistry.

The dielectrics of this invention usually comprise 2 to 15, preferably 3 to 12, components, at least one of which is a compound of formula I. The other constituents are preferably chosen from the nematic or nematogenic substances, in particular the known substances, from the classes of azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyl-dioxanes, optionally halogenated stilbenes, benzylphenyl ethers, tolans and substituted cinnamic acids. The most important compounds which can be used as constituents of such liquid crystal dielectrics can be characterized by formula VI

    R³—A—G—E—R⁴    VI wherein A and E are each a carbocyclic or heterocyclic ring system from the group comprising 1,4-disubstituted benzene or cyclohexane rings, 4,4'-disubstituted biphenyl, phenylcyclohexane or cyclohexylcyclohexane systems, 2,5-disubstituted pyrimidine or 1,3-dioxane rings, 2,6-disubstituted naphthalene, di- or tetra-hydronaphthalene, quinazoline and tetrahydroquinazoline, G is —CH═CH—, —CH═CL—, —C≡C—, —CO—O—, —CO—S—, —CN═N—, —N(O)═N—, —CH═N(O)—, —CH₂—CH₂—, —CH₂—O—, —CH₂—S—, —COO—Ph—COO— or a C—C single bond, L is halogen, preferably chlorine, or CN, and R³ and R⁴ are alkyl, alkoxy, alkanoyloxy or alkoxycarbonyloxy with up to 18, preferably up to 8, carbon atoms, or one of these radicals is CN, NC, NO₂, CF₃, F, Cl or Br. In most of these compounds, R³ and R⁴ differ from one another, one of these radicals usually being alkyl or alkoxy. Many such substances or mixtures thereof are commercially available.

The dielectrics according to this invention contain about 0.1 to 30%, preferably 2 to 25%, of one or more compounds of formula I.

The dielectrics according to this invention are prepared in a manner which is customary per se. As a rule, the components are dissolved in one another, preferably at elevated temperature. If a temperature above the clear point of the main constituent is thereby chosen, it is particularly easy to observe the completion of the solution operation.

The liquid crystal dielectrics of this invention can be modified by suitable additives such that they can be used in all the types of liquid crystal display elements which have hitherto been disclosed.

Such additives are familiar to the expert and are described in detail in the literature. For example, dichroic dyestuffs or substances for modifying the dielectric anisotropy, the viscosity, the conductivity and/or the orientation of the nematic phases can be added. Such substances are described in, for example, German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

EXAMPLE 1

35.2 g of trans, trans-4'-propyl-bicyclohexyl-4-carboxylic acid is boiled with 24 g of SOCl₂ for 1 hour; the mixture is evaporated; the resulting crude acid chloride is dissolved in 150 ml of toluene; 7.9 g of pyridine and 6 g of propanol are added; and the mixture is boiled for 2 hours. The mixture is cooled and washed with water and the organic phase is dried over Na₂SO₄ and evaporated. Propyl trans, trans-4'-propylbicyclohexyl-4-carboxylate of m.p. 24° and c.p. 54° is obtained.

EXAMPLES 2 to 43

The following compounds are obtained analogously to Example 1 by esterifying the corresponding carboxylic acids via the corresponding acid chlorides:

2. Ethyl trans,trans-4'-ethyl-bicyclohexyl-4-carboxylate.
3. R-2-Methylbutyl trans,trans-4'-ethyl-bicyclohexyl-4-carboxylate.
4. S-2-Methylbutyl trans,trans-4'-ethyl-bicyclohexyl-4-carboxylate.
5. R-2-Octyl trans,trans-4'-ethyl-bicyclohexyl-4-carboxylate.
6. S-2-Octyl trans,trans-4'-ethyl-bicyclohexyl-4-carboxylate.
7. Ethyl trans,trans-4'-propyl-bicyclohexyl-4-carboxylate.
8. Butyl trans,trans-4'-propyl-bicyclohexyl-4-carboxylate of m.p. 25° and c.p. 41°.
9. Pentyl trans,trans-4'-propyl-bicyclohexyl-4-carboxylate.
10. R-2-Methylbutyl trans,trans-4'-propyl-bicyclohexyl-4-carboxylate.
11. S-Methylbutyl trans,trans-4'-propyl-bicyclohexyl-4-carboxylate.

12. R-2-Octyl trans,trans-4'-propyl-bicyclohexyl-4-carboxylate.
13. S-2-Octyl trans,trans-4'-propyl-bicyclohexyl-4-carboxylate.
14. Octyl trans,trans-4'-propyl-bicyclohexyl-4-carboxylate.
15. Trifluoromethyl trans,trans-4'-propyl-bicyclohexyl-4-carboxylate.
16. Pentafluoroethyl trans,trans-4'-propyl-bicyclohexyl-4-carboxylate.
17. Heptafluoropropyl trans,trans-4'-propyl-bicyclohexyl-4-carboxylate.
18. Nonafluorobutyl trans,trans-4'-propyl-bicyclohexyl-4-carboxylate.
19. trans-4-(trans-4-Propylcyclohexyl)-cyclohexyl trans,trans-4'-propyl-bicyclohexyl-4-carboxylate.
20. trans-4-p-Methoxyphenyl-cyclohexyl trans,trans-4'-propyl-bicyclohexyl-4-carboxylate.
21. p-trans-4-Pentylcyclohexyl-phenyl trans,trans-4'-propyl-bicyclohexyl-4-carboxylate.
22. 4'-Propoxy-4-biphenylyl trans,trans-4'-propyl-bicyclohexyl-4-carboxylate.
23. Ethyl trans,trans-4'-butyl-bicyclohexyl-4-carboxylate.
24. Propyl trans,trans-4'-butyl-bicyclohexyl-4-carboxylate.
25. Pentyl trans,trans-4'-butyl-bicyclohexyl-4-carboxylate.
26. R-2-Methylbutyl trans,trans-4'-butyl-bicyclohexyl-4-carboxylate of c.p. 47°.
27. S-2-Methylbutyl trans,trans-4'-butyl-bicyclohexyl-4-carboxylate.
28. R-2-Octyl trans,trans-4'-butyl-bicyclohexyl-4-carboxylate, b.p. 210° C./0.2 bar.
29. S-2-Octyl trans,trans-4'-butyl-bicyclohexyl-4-carboxylate.
30. Ethyl trans,trans-4'-pentyl-bicyclohexyl-4-carboxylate.
31. Propyl trans,trans-4'-pentyl-bicyclohexyl-4-carboxylate of m.p. 37° and c.p. 79°.
32. Pentyl trans,trans-4'-pentyl-bicyclohexyl-4-carboxylate.
33. R-2-Methylbutyl trans,trans-4'-pentyl-bicyclohexyl-4-carboxylate.
34. S-2-methylbutyl trans,trans-4'-pentyl-bicyclohexyl-4-carboxylate.
35. R-2-Octyl trans,trans-4'-pentyl-bicyclohexyl-4-carboxylate.
36. S-2-Octyl trans,trans-4'-pentyl-bicyclohexyl-4-carboxylate.
37. Ethyl trans,trans-4'-heptyl-bicyclohexyl-4-carboxylate.
38. Propyl trans,trans-4'-heptyl-bicyclohexyl-4-carboxylate.
39. Pentyl trans,trans-4'-heptyl-bicyclohexyl-4-carboxylate.
40. R-2-Methylbutyl trans,trans-4'-heptyl-bicyclohexyl-4-carboxylate.
41. S-2-Methylbutyl trans,trans-4'-heptyl-bicyclohexyl-4-carboxylate.
42. R-2-Octyl trans,trans-4'-heptyl-bicyclohexyl-4-carboxylate.
43. S-2-Octyl trans,trans-4'-heptyl-bicyclohexyl-4-carboxylate.

EXAMPLE 44

Trans, trans-4'-butyl-bicyclohexyl 4-butyrate of m.p. 24° and c.p. 86° is obtained analogously to Example 1, from butyryl chloride and trans, trans4'-butyl-bicyclohexyl- 4-ol (which can be prepared by hydrogenation of p-trans-4-butylcyclohexyl-phenol and subsequent isomer separation).

EXAMPLES 45 to 64

The following compounds can be obtained analogously to Example 44:

45. trans,trans-4'-Methyl-bicyclohexyl 4-acetate.
46. trans,trans-4'-Ethyl-bicyclohexyl 4-acetate.
47. trans,trans-4'-Ethyl-bicyclohexyl 4-propionate.
48. trans,trans-4'-Ethyl-bicyclohexyl 4-butyrate.
49. trans,trans-4'-Ethyl-bicyclohexyl 4-caproate.
50. trans,trans-4'-Propyl-bicyclohexyl 4-acetate.
51. trans,trans-4'-Propyl-bicyclohexyl 4-propionate.
52. trans,trans-4'-Propyl-bicyclohexyl 4-butyrate.
53. trans,trans-4'-Propyl-bicyclohexyl 4-caproate.
54. trans,trans-4'-Butyl-bicyclohexyl 4-acetate.
55. trans,trans-4'-Butyl-bicyclohexyl 4-propionate.
56. trans,trans-4'-Butyl-bicyclohexyl 4-caproate.
57. trans,trans-4'-Pentyl-bicyclohexyl 4-acetate.
58. trans,trans-4'-Pentyl-bicyclohexyl 4-propionate.
59. trans,trans-4'-Pentyl-bicyclohexyl 4-butyrate of m.p. 33° and c.p. 93°.
60. trans,trans-4'-Pentyl-bicyclohexyl 4-caproate.
61. trans,trans-4'-Heptyl-bicyclohexyl 4-acetate.
62. trans,trans-4'-Heptyl-bicyclohexyl 4-propionate.
63. trans,trans-4'-Heptyl-bicyclohexyl 4-butyrate.
64. trans,trans-4'-Heptyl-bicyclohexyl 4-caproate.

EXAMPLE 65

A mixture of 3.56 g of p-[trans-4-(trans-4-propylcyclohexyl)-cyclohexylcarbonyloxy]-benzaldehyde (obtainable by acylation of p-hydroxybenzaldehyde), 1.32 g of 2-butylpropane-1,3-diol, 0.01 g of p-toluenesulfonic acid and 20 ml of toluene is boiled for 4 hours, using a water separator, and is cooled, washed with water and evaporated. 5-butyl-2-p-[trans-4-(trans-4-propylcyclohexyl)-cyclohexyl-carbonyloxy]-phenyl-1,3-dioxane is obtained.

The examples which follow are those of dielectrics of this invention, containing at least one compound of formula I:

EXAMPLE A

A mixture of
20% of propyl trans, trans-4'-pentyl-bicyclohexyl-4-carboxylate
25% of p-(trans-4-propyl-cyclohexyl)-benzonitrile
20% of trans, trans-4'-butyl-bicyclohexyl-4-carbonitrile
18% of p-(trans-4-propyl-cyclohexyl)-ethoxybenzene and
17% of p-trans-4-propylcyclohexyl-phenyl trans 4-pentylcyclohexane carboxylate
has an m.p. of 0° and a c.p. of 58°.

EXAMPLE B

A mixture of
2% of S-2-octyl trans, trans-4'-butylbicyclohexyl-4-carboxylate
22% of p-trans-4-propylcyclohexyl-benzonitrile
36% of p-trans-4-pentylcyclohexyl-benzonitrile
25% of p-trans-4-heptylcyclohexyl-benzonitrile and
15% of 4'-(trans-4-pentylcyclohexyl)-biphenyl-4-carbonitrile
has an m.p. of −5° and a c.p. of 69°.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bicyclohexyl derivative of the formula $$R^1-Cy-Cy-X-y$$

wherein
X is —CO—O— or O—CO—,
Y is alkyl or perfluoroalkyl each of 1-8 C atoms, or —Ph—Dio—$R^2$,
Cy is 1,4-cyclohexylene,
Ph is 1,4-phenylene,
Dio is 1,3-dioxane-2,5-diyl and
$R^1$ and $R^2$ are each independently alkyl or alkoxy each of 1-8 C atoms.

2. A compound of claim 1 of the formula
$R^1$-Cy-Cy-CO-O-perfluoroalkyl
$R^1$-Cy-Cy-O-CO-perfluoroalkyl
$R^1$-Cy-Cy-O-CO-Ph-Dio-$R^2$, or
$R^1$-Cy-Cy-CO-O-Ph-Dio-$R^2$ 3. A compound of claim 1 of the formula
$R^1$-Cy-Cy-CO-O-alkyl or
$R^1$-Cy-Cy-O-CO-alkyl.

4. A compound of claim 1 wherein $R^1$ and $R^2$ or $R^1$ and Y are both alkyl.

5. A compound of claim 1 wherein all alkyl, perfluoroalkyl and alkoxy groups are of 1-5 C atoms.

6. A compound of claim 1 wherein all alkyl, alkoxy and perfluoroalkyl groups are straight chained.

7. A liquid crystal dielectric useful in electooptical display elements and comprising at least two liquid crystal components, wherein at least one such component is a bicyclohexyl derivative of the formula $$R^1-Cy-Cy-X-Y$$

wherein
X is —CO—O— or O—CO—,
Y is alkyl or perfluoroalkyl each of 1-8 C atoms, or —Ph—Dio—$R^2$,
Cy is 1,4-cyclohexylene,
Ph is 1,4-phenylene,
Dio is 1,3-dioxane-2,5-diyl and
$R^1$ and $R^2$ are each independently alkyl or alkoxy each of 1-8 C atoms.

8. A dielectric of claim 7 comprising 2-15 components.

9. A dielectric of claim 7 wherein the amount of said bicyclohexyl derivative is 0.1-30 wt %.

10. In an electrooptical display element comprising a liquid crystal cell containing a liquid crystal dielectric, the improvement wherein the dielectric is that of claim 7.

11. An electrooptical display element of claim 10 wherein the dielectric comprises 2-15 components.

12. A liquid crystalline dielectric of claim 7 wherein X is O—CO— and y is perfluoroalkyl of 1-8 C atoms, or —Ph—Dio—$R^2$; or X is —CO—O— and Y is alkyl or perfluoroalkyl each of 1-8 C atoms, —Cy—Cy—$R^2$, —Cy—Ph—$R^2$, —Ph—Cy—$R^2$, —Ph—Ph—$R^2$ or —Ph—Dio—$R^2$.

13. A liquid crystalline dielectric of claim 12 wherein said derivative is of the formula
$R^1$—Cy—Cy—CO—O-perfluoroalkyl
$R^1$—Cy—Cy—CO—O—Ph—Dio—$R^2$
$R^1$—Cy—Cy—O—CO-perfluoroalkyl or
$R^1$—Cy—Cy—O—CO—Ph—Dio—$R^2$.

14. A liquid crystalline dielectric of claim 12 wherein said derivative is of the formula $$R^1-Cy-Cy-CO-O-alkyl.$$

15. A liquid crystalline dielectric of claim 12 wherein $R^1$ and $R^2$ or $R^1$ and Y are both alkyl.

16. A liquid crystalline dielectric of claim 12 wherein all alkyl, perfluoroalkyl and alkoxy groups are of 1-5 C atoms.

17. A liquid crystalline dielectric of claim 12 wherein all alkyl, alkoxy and perfluoroalkyl groups are straight chained.

18. A liquid crystalline dielectric of claim 12 wherein Y is perfluoroalkyl of 1-8 C atoms, or —Ph—Dio—$R^2$.

19. A compound of claim 1 wherein Y is perfluoroalkyl of 1-8 C atoms or —Ph—Dio—$R^2$.

20. A compound of claim 1 of the formula $$R^1-Cy-Cy-O-CO\text{-alkyl}.$$

21. A liquid crystalline dielectric of claim 7 wherein said derivative is of the formula $$R^1-Cy-Cy-O-CO\text{-alkyl}.$$

* * * * *